United States Patent [19]
Bryars

[11] Patent Number: 5,509,423
[45] Date of Patent: Apr. 23, 1996

[54] PUMP BAND

[75] Inventor: John D. Bryars, Encinitas, Calif.

[73] Assignee: Advanced Bodymetrics Corporation, Rancho Santa Fe, Calif.

[21] Appl. No.: 174,266

[22] Filed: Dec. 28, 1993

[51] Int. Cl.⁶ ............................................... A61B 5/0245
[52] U.S. Cl. ............................................................ 128/690
[58] Field of Search ................................. 128/672, 686, 128/687–690

[56] References Cited

U.S. PATENT DOCUMENTS

| | | | |
|---|---|---|---|
| 2,753,863 | 7/1956 | Bailey | 128/686 X |
| 4,549,550 | 10/1985 | Kami | 128/686 |
| 4,862,895 | 9/1989 | Yamasawa et al. | 128/686 X |
| 4,867,170 | 9/1989 | Takahashi | 128/690 X |
| 4,947,855 | 8/1990 | Yokoe et al. | 128/687 X |
| 5,158,091 | 10/1992 | Butterfield et al. | 128/687 X |

*Primary Examiner*—Angela D. Sykes
*Attorney, Agent, or Firm*—G. Donald Weber, Jr.

[57] ABSTRACT

A pneumatic pump assembly adapted to be integrated into a device for monitoring heart pulse rates from radial arterial sources. The pump assembly includes a pneumatic pump with a bulb component, a self-sealing flapper valve and a tube connecting the pump with an inflatable bladder. Sensors are disposed at the bladder whereby they can be oriented with regard to the radial artery of the wearer upon inflation or release of air pressure in the bladder. Typically, the pump assembly and monitoring device are worn at the wrist of the user.

17 Claims, 2 Drawing Sheets

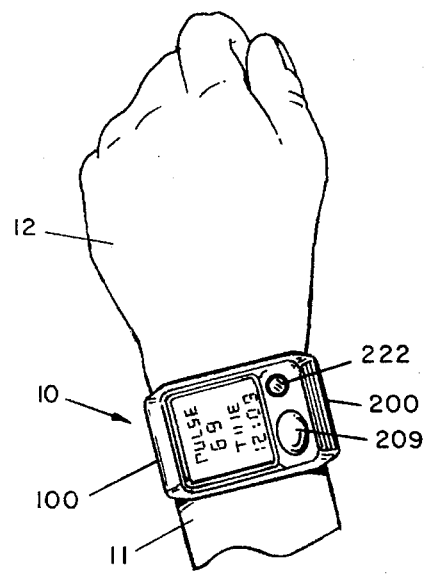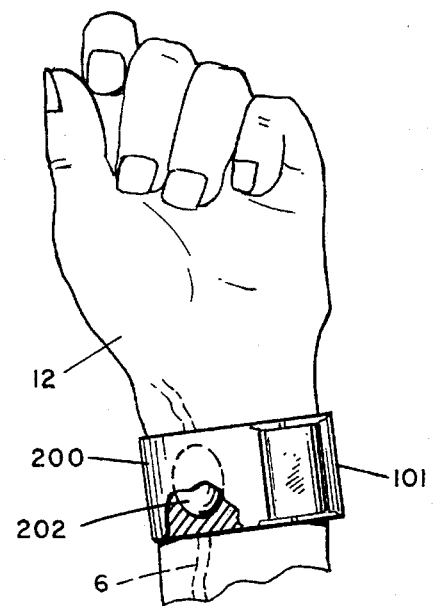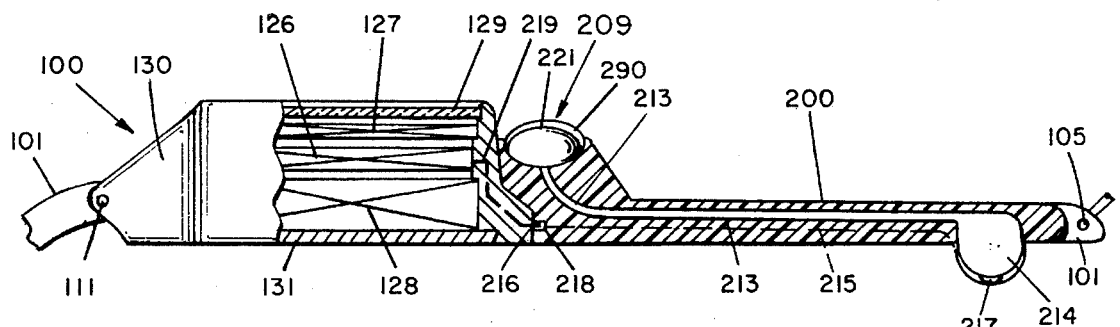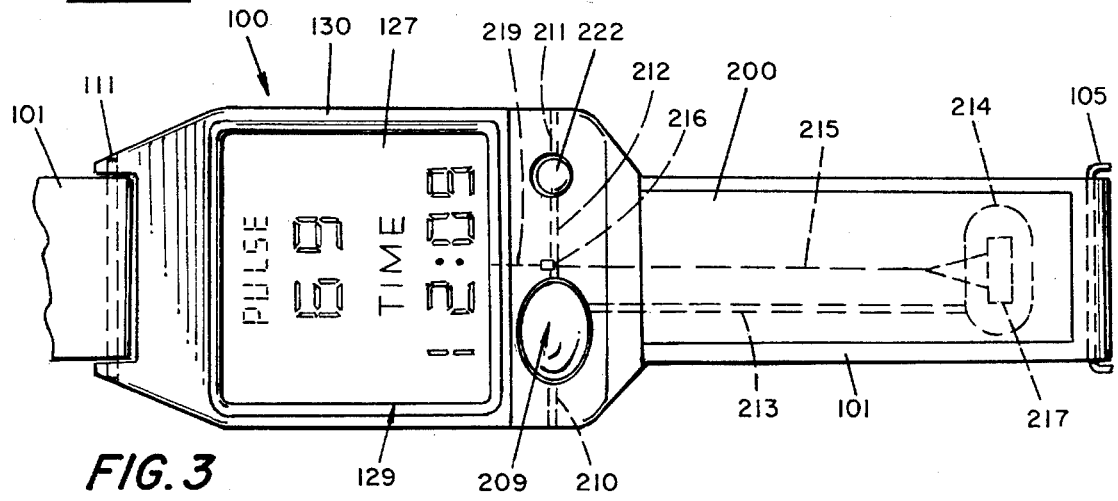

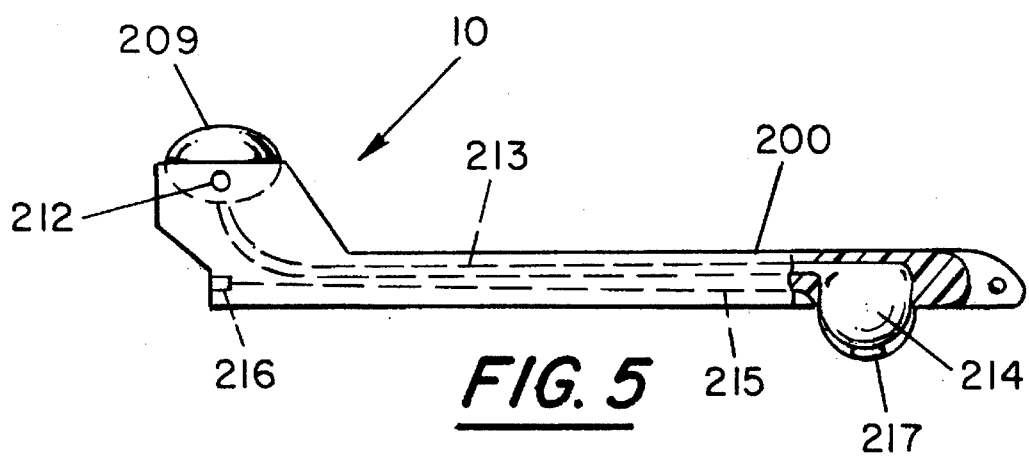
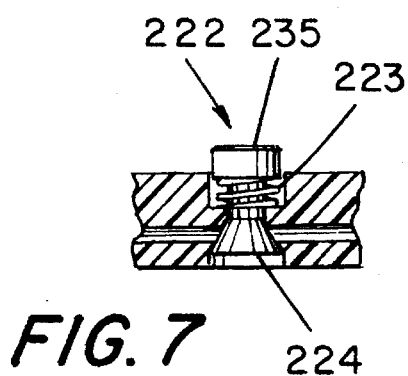
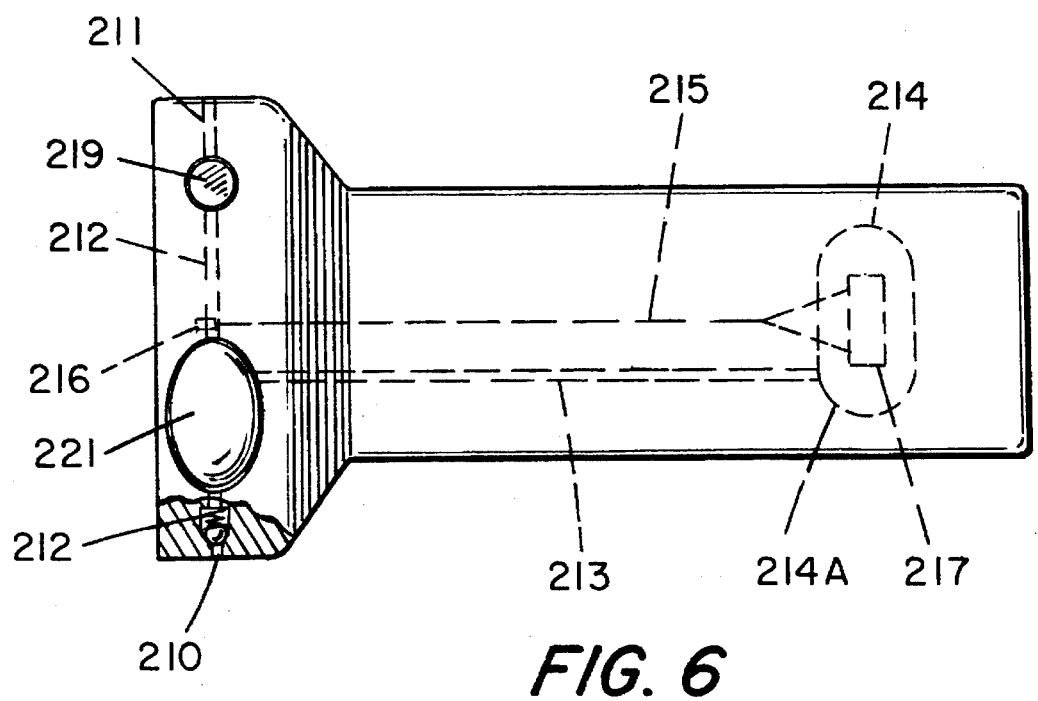

PUMP BAND

BACKGROUND

1. Field of the Invention

This invention relates to cardiac pulse rate monitoring devices, in general, and, more particularly, to a novel apparatus including a self-contained pump assembly for selectively positioning sensors in such monitoring devices.

2. Prior Art

Health and fitness is a relatively common concern and goal of many persons. One method of fulfilling these objectives is exercise. Electronic equipment for the monitoring of a person's heart pulse activity is employed in health care institutions and by persons during athletic training.

One important measurement parameter is the rate of occurrence of heart pulsations. In healthy persons, the pulse rate is substantially uniform throughout the duration of a person's normal activity. However, the rate varies with changes in the person's activity when the heart may be called upon to pump at a higher or lower rate. The rate of pulse change during increasing or decreasing activity is directly related to a person's physical condition.

Thus, it must be appreciated that a device providing an accurate measurement of pulse rate is most useful during athletic training and for the detection and treatment of disease. Heart rate monitoring can be used to guide cardiovascular intensity to achieve maximum fitness results within any aerobic exercise regimen. The measurement of heart pulse rate is usually accomplished by an electronic unit worn by the individual. These units are worn on various parts of the body, most typically on the wrist. However, wearing the unit on the wrist usually necessitates the use of complex miniature electronic equipment.

That is, accurate measurement of an active person's pulse rate at the wrist is a complex process due to the artifacts produced by body motion. These artifacts are produced concurrent with the heart pulse and are, typically, detected by the heart pulse sensor as noise. However, in many cases, the artifacts produce signals of sufficient amplitude to completely mask the desired heart pulse signal. In order to mitigate the effects of these body artifacts, it is necessary to filter out and electrically cancel as much of the noise signal occurring in the heart pulse frequency band as possible while retaining the desired pulse signal.

This problem must be dealt with effectively over a considerable signal-to-noise ratio range. In some extreme cases, the signal-to-noise ratio will become negative even with very effective cancellation techniques. When it is no longer possible to reliably detect the heart pulse rate, it is necessary that no attempt is made to display a heart rate reading due to the high probability of introducing inaccuracies. It is better to store and display the last good reading until the severe noise condition is over and an accurate reading can be made.

However, during monitoring sequences, it is important that the user be able to frequently receive accurate updates of the heart pulse rate. It has been demonstrated that this should occur no more frequently than every five seconds with an update every ten seconds seeming to be optimal. This is important to the user since even in situations where violent physical activity is creating body artifact noise in excess of what can be tolerated by the system, only a short, relatively still period would be required to provide an updated readout of pulse rate.

Several devices have been proposed for providing a wrist watch type of heart pulse monitor. One such device is the digital plethysmography described in Prinz (U.S. Pat. No. 4,120,269), which customarily utilizes an infrared light transducer. Other devices have proposed using piezoelectric or other pressure sensitive transducers, such as in Stupay (U.S. Pat. No. 4,059,118), which uses an actuator pin pressing against a piezoelectric crystal.

Typically, such devices tend to have several shortcomings. Devices using optical transducers, such as the digital plethysmographies, consume substantial power in the light emitting elements and, thus, use up battery life rapidly. Devices using piezoelectric transducers, such as Stupay, typically devote little attention to the substantial noise problems that attend the use of such transducers in this application.

When such a pulse rate monitor is mounted on the wearer's wrist, the pulse signal is, to a significant extent, masked by the concurrent noise signals generated due to body motions. The mechanical transducer responds to, but does not distinguish between, pressure from the wearer's pulse beat or motion from walking, arm swinging and the like. The latter is noise insofar as pulse measurement is concerned. Thus, the user of the piezoelectric transducer system must remain quiet to avoid noise input" during the period in which the pulse rate is being measured.

Also, if the piezoelectric transducer is not mounted directly over the artery of the user, the pulse signal measured by the device will be significantly reduced in amplitude. This signal is, thus, even more likely to be masked by noise. Typically, noise signals may be as high as 1.0 volt, while the pulse signal may be approximately 0.1 volt. Prior art wrist pulse rate monitors employing piezoelectric transducers have been inaccurate because of this unfavorable signal-to-noise ratio. Thus, Cramer (U.S. Pat. No. 4,224,948) teaches that when a piezoelectric sensor is used, the monitor must be worn on the volar surface of the wrist but lateral to the tendon chord bundles so as to obtain a pulse reading from the radial artery in the subpollex depression. In this case, the sensors must be forced into the flesh of the wrist for a reading which may be uncomfortable.

Albert (U.S. Pat. No. 4,409,983) uses a complex arrangement of piezo sensors to develop relatively noise-free signals which are presented to the input of a microprocessor. This device employs a piezo sensor which is operated by providing a bending force to one end of the sensor element. This bending interaction is accomplished by using small pins pushing against the ends of the sensors with coil springs used to dampen the high frequency noise products. Algebraic analog signal summing is used to create relatively noise-free signals at the input to the microprocessor in the form of an electrical pulse string having the same rate as the heart pulse. While this device may reduce the attendant body noise, the complexity of the sensor system makes this arrangement impractical for mass production.

Monitoring systems using optical sensors to detect the heart rate pulse at the radial artery on the wrist tend to have many of the same body motion related problems as the piezo sensor systems. Added to the motion-induced noise problems is the introduction of noise artifacts that are caused by ambient light conditions. These noise sources can be any electrical or natural light sources such as the sun. However, optical sensors do not tend to detect body transmitted acoustical noise. An effective method of dealing with these noise sources is necessary in order to make accurate heart pulse rate readings when the body is in motion or exposed to changing lighting conditions.

PRIOR ART STATEMENT

A formal patentability search was not conducted. However, the best known available prior art is described above.

SUMMARY OF THE INSTANT INVENTION

This invention provides a self-contained pneumatic pump assembly that is integratable into a support unit, such as a wrist band, to be utilized in conjunction with a heart rate pulse monitor. In one embodiment, the monitor is integrated into the housing of a watch. The pump assembly allows sensors associated with the assembly to be positioned so that they are able to detect the heart rate pulse from an arterial source in the wrist of the user. Pulse rate information from the sensors is transmitted to the monitor for processing and digital readout display purposes.

The pump assembly consists of a small, bulb-type pneumatic pump having a self-sealing inlet flapper valve, a bladder with sensors mounted thereat, an airway tube between the bulb and the bladder, and a relief valve.

When the bulb is depressed, the flapper valve is closed and air is forced through the tube into the sensor bladder. When the pump is released, the flapper valve opens and the pump becomes filled with air. Several actuations of the pump may be required to sufficiently inflate the bladder for proper positioning of the sensors. When there is sufficient pressure in the system, the amount of air returning to the pump bulb from the sensor bladder will be equal to or greater than the air coming from the outside. When this occurs, no more air can be pumped into the sensor bladder. This feature prevents blowing out bladders and pumps. Likewise, when the pump bulb is released and the pump system is filled with air, this pressure will be maintained until the pressure relief valve is operated and the air in the bladder is released back into the atmosphere.

BRIEF DESCRIPTION OF THE DRAWINGS

FIG. 1 is a plan view of a representative monitor assembly which includes the pump assembly of the instant invention.

FIG. 2 is a plan view of the embodiment shown in FIG. 1, rotated 180°.

FIG. 3 is a partially sectioned, partially broken away elevational view of the monitor and pump assembly of the instant invention.

FIG. 4 is a partially sectioned, partially broken away plan view of the monitor and pump assembly of the instant invention.

FIG. 5 is a more detailed view of the pump assembly shown in FIG. 3.

FIG. 6 is a more detailed view of the pump assembly shown in FIG. 4.

FIG. 7 is a partially sectioned, partially broken away view of the relief valve assembly of the instant invention.

DESCRIPTION OF A PREFERRED EMBODIMENT

Referring now to FIG. 1, there is shown a plan view of one embodiment of a monitor which includes a pump accessory, as defined by the instant invention.

In FIG. 1, a monitor 10 is shown worn or mounted on the body of the user. In particular, the monitor 10 is mounted at the wrist 11 of the hand 12 of the user. In this embodiment, the monitoring apparatus is mounted at the back or outer portion of the wrist. The monitor 10 may include any number of display devices (see infra) including a wrist watch or the like. The monitor 10 also includes the monitoring apparatus 100 which is mounted in a conventional manner to a wrist band 101 and a pump assembly 200 which is connected to the band 101 as described hereinafter.

The pump apparatus 200 includes a relief valve 222 and a pump 209 which are interconnected as described infra. As will be described hereinafter in FIG. 2, the pump 209 and the relief valve 222 are also connected to the bladder 202.

Referring now to FIG. 2, there is shown a plan view of the monitoring apparatus shown in FIG. 1 with the hand 12 of the user rotated 180° to show the interior or front of the wrist.

In this case, the band 101 is connected to the monitor 100 in a conventional manner, e.g. pins can pass through loops in the band. The ends of band 101 can be joined together by a suitable clasp 105 such as a metallic clasp, a ring, a hook and loop arrangement (frequently sold under the trademark Velcro) or the like. The pump assembly 200 is mounted within the band 101. For example, an opening or a cavity may be provided or found in the band 101. The pump assembly 200 includes the bladder 202 which is shown partially in dashed section and, partially broken away. The bladder 202 is, typically, a flexible, expandable material. As shown in FIG. 2, the bladder 200 (which includes sensors as described infra) is disposed at the inside of the assembly 200 and arranged to be above or adjacent to the radial artery 106 (shown in dashed outline) of the user.

Referring now to FIG. 3, there is shown a partially sectioned, partially broken away elevational view of the monitor and pump assembly of the instant invention.

In particular, the monitor 100 includes a housing 130 which is attached to the wrist band 101 by any suitable means such as pins 111 which pass through the ends of the band 101 and are engaged by the housing 130 in a conventional manner.

The housing or case 130 includes a face or display 127 which can, in a preferable embodiment, provide a digital output display, as described hereinafter. A typical, although not limitative, display apparatus is a liquid crystal display (LCD) device. In the embodiment shown, the display device is designed to display the time as well as the pulse rate. Other parameters can be measured and displayed, as well. A face crystal 129 can be disposed over the face of the monitor 100 for protection.

In a preferred embodiment, the pump assembly 200 is made of a strong, yet flexible, material such as neoprene, flexible plastic or the like which is of similar consistency to the band. Typically, the pump assembly 200 is a separate unit which is embedded into the wrist band 101 which encircles the wrist of the user. The assembly can be glued in place in the band, for example. The band 101 and assembly 200 are chemically and aesthetically compatible. In this instance, the band includes the clasp 105 which engages the other portion of the band 101 as suggested in FIG. 2.

The pump assembly 200, per se, can include a pump mechanism 209 in the nature of a flexible diaphragm or bellows-like arrangement. In a typical arrangement, a relatively thin, air-impervious membrane is mounted at the upper surface of the pump assembly to form a pump 209. The membrane can extend upwardly from the upper surface assembly of the pump surface. Alternatively, the membrane can be disposed over a cavity in the pump assembly. Of course, a combination of these structures can be utilized. The pump 209 is selectively operated when the membrane is flexed by the user to effect a pumping operation.

The pump 209 (including the open area under the membrane or bellows) is connected to receive input air through an air tube 210 during the pumping operation. A flapper valve 219 selectively opens and closes the air tube 210 to the passage of air therethrough in conjunction with the operation of the pump 209.

A relief valve 222 is also provided in the pump assembly 200. A conduit 212 interconnects the pump 209 and the relief valve 222. The relief valve 222 includes an exit air tube 211 which is vented to ambient in order to selectively remove air from the pump and the system, as described hereinafter.

A bladder 214 is disposed at the other end of the pump assembly, typically, on the underside. The bladder 214 also can take the form of a relatively flexible portion of rubber, neoprene or the like formed in the pump. The bladder 214 is, typically, disposed co-planar with the underside of the assembly 200.

The pump 209 and the bladder 214 are connected together by a suitable conduit 213. Thus, by action of the pump 209, air can be pumped from tube 210 through tube 213 into bladder 214. The pumping action causes the bladder 214 to expand, as described hereinafter. Conversely, air can be deleted from bladder 214 along tube 213, pump 209, tube 212, relief valve 222 and vent tube 211.

A suitable sensor 217 can be mounted in or at the surface of bladder 214. The sensor 217 can be piezoelectric, optical or any other suitable sensor, as described supra. The sensor 217 is connected to an electronic circuit or wire cable 215. The electronic wiring 215 can be molded directly into the pump assembly 200 or formed on the surface thereof in any suitable fashion.

The wiring 215 is connected to a connector 218 in the end of assembly 200 and which mates with a connector 216 provided in the monitor 100. The connector 216 is connected via a separate conductor line 219 to the electronics portion of the monitor 100.

Referring now to FIG. 4, there is shown a partially sectioned, partially broken away elevational view of the monitor and pump assembly of the instant invention. In this partially broken away view, the watch crystal 129 is shown at the upper surface of the monitor 100. A backplate 131 is provided at the bottom and may form a portion of the actual housing of case 130. These arrangements are conventional.

Inside the monitor 100 is a power source or battery 128 which is conventional. Suitable electronic circuitry 126 is also provided in the housing and is connected to the battery in a conventional manner to be powered thereby. The electronic circuitry 126 is connected to the electronic conductor 219 and the connector 216 as described relative to FIG. 3.

A liquid crystal display 127 (or similar display device) is connected to the electronic circuitry 126 and driven thereby to provide the output signals and/or display. As noted above, the LCD 127 can produce time signals, pulse rate signals and the like.

As suggested, the connector 216 in the monitor is connected to the connector 218 is the pump assembly. The connector 218 is connected to the conductors 215, which are connected to the sensor means 217 in the bladder 214 in the pump 200.

The air tube 213 is connected between the pump or bellows 209 and the bladder 214 wherein air is pumped from the pump to the bladder.

In FIG. 4, the bladder 214 is shown in the extended or expanded position with the sensor 217 at the surface thereof.

As noted above, in the rest position, with the air released, the bladder 214 will retract approximately coplanar with the bottom surface of the pump assembly.

Referring now to FIG. 5, there is shown a more detailed, cross-sectional view of the pump assembly 200 without the monitor 100 or the band 101. In this case, the pump 209 is shown as a bulb-type bellows which is connected to the bladder 214 by the air tube 213. Again, the bladder 214 is shown in the expanded position. The sensor 217 (which is representative only) is shown mounted on the outer surface of bladder 214. The sensor 217 is connected to the electrical wiring 215, which is then connected to connector 216, which may be in the form of a pin or the like.

As shown in FIG. 5, the pump bulb communicates with plenum 221 directly beneath the bulb 209. The plenum communicates with the air tube 213 and with the air tube 212 which is connected to the relief valve 212.

Referring now to FIG. 6, there is shown a more detailed plan view of the pump assembly 200. The pump/bellows plenum 221 communicates, via air tube 212, with the relief valve 211 and the air exhaust tube 211.

The plenum 221 also communicates with air tube 213 which communicates with the bladder 214 and its associated plenum 214A. The sensor 217 is located on the bladder 214 in any suitable fashion. The sensor 217 is connected to the connector 216, as described above. The plenum 221 includes a flapper valve 212 which takes the form of a flap formed over the air inlet tube 221.

In operation, the pump 209 is actuated by pressing the bulb 209. This action forces air from the plenum 221 through air tube 213 into the plenum 214A and the bladder 214. In this instance, the force or pressure on the air in the plenum 221 also forces the flap 212 against the opening of air inlet 210 which is, thus, sealed.

In this operation, it is assumed that the relief valve 211 is closed and does not permit airflow through air tube 212. The pump action can be repeated. When the pump 209 is released after a first pumping manuever, the pressure on the inside of the plenum 221 and the valve 212 is insufficient to prevent air from entering the plenum through air tube 290. The pumping exercise is then repeated until the appropriate pressure is obtained at bladder 214.

The purpose of inflating bladder 214 with sensors 217 thereon is to force the bladder into the subpollex depression on the wrist of the user in order to obtain a more accurate association with the radial artery in the wrist.

Of course, if a different characteristic is being monitored or if the the monitor is to be worn at the ankle, adjacent the temporal artery or any other body part, other adjustments may be desirable.

Referring now to FIG. 7, there is shown a cross-sectional view of the relief valve 219. In this embodiment, the relief valve includes an actuator 235, which is in the form of a plunger which includes a seat 224. The actuator has a coil spring 223 wrapped around the plunger portion thereof. The spring-loaded plunger is mounted in an aperture in the upper surface of the pump assembly. Typically, the seat 224 is arranged to seal the aperture through the body of the pump assembly in response to the action of coil spring 223. When it is desired to release air from the bladder 214 via air tube 213, plenum 221 and air tube 212, the actuator 235 of relief valve 219 is pressed inwardly against the action of coil spring 223. This operation opens the aperture 222 through the pump assembly wherein air is exhausted through air tube 211.

Thus, there is shown and described a unique design and concept of an apparatus designed for pulse rate monitoring.

Of course, other characteristics such as blood pressure, blood oxygenation or the like can be monitored. The particular configuration shown and described herein relates to a self-contained pump assembly which is integratable into a wrist watch band. It is contemplated that the monitor can be mounted elsewhere than the wrist. Moreover, the monitor is not limited to use with humans. While this description is directed to a particular embodiment, it is understood that those skilled in the art may conceive modifications and/or variations to the specific embodiments shown and described herein. Any such modifications or variations which fall within the purview of this description are intended to be included therein as well. It is understood that the description herein is intended to be illustrative only and is not intended to be limitative. Rather, the scope of the invention described herein is limited only by the claims appended hereto.

I claim:

1. A pneumatic pump assembly including, support means, pump means formed in said support means, an inlet valve in said support means for selectively admitting fluid into said pump means, said inlet valve adapted to be self-sealing when pressure is applied to said pump means whereby fluid in said pump means is not passed through said inlet valve, a pressure relief valve in said support means to selectively pass fluid therethrough from said pump means, bladder means mounted in said support means, said bladder means connected to receive fluid from said pump means and be inflated thereby when pressure is applied to said pump means, and sensor means mounted to said bladder means such that the positional orientation of said sensor means is dependent upon the inflation level of said bladder means.

2. The pump band recited in claim 1 wherein, said sensor means comprises optical sensors.

3. The pump band recited in claim 1 including, strap means said pneumatic pump assembly comprises a unitary assembly unit which is selectively detachable from said support means.

4. The pump band recited in claim 3 wherein, said support means is made of metal.

5. The pump band recited in claim 3 wherein, said support means is made of leather.

6. The pump band recited in claim 3 wherein, said support means is made of rubber.

7. The pump band recited in claim 3 wherein, said support means is made of plastic.

8. The pump band recited an claim 3 including, electronic assembly means for monitoring heart pulse rate signals mounted to said support means.

9. The pump band recited in claim 8 including, electrical conductor means in said support means connected from said sensor means to said electronic assembly means.

10. The pump band recited in claim 8 wherein, said electronic assembly includes an electronic power source.

11. The pump band recited in claim 8 wherein, said electronic assembly includes a readout display means.

12. The pump band recited in claim 11 wherein, said display means is a liquid crystal display.

13. The pump band recited in claim 1 wherein, said pressure relief valve includes a press button actuator.

14. The assembly recited in claim 1 wherein, said bladder means selectively extends outwardly from said support means.

15. The assembly recited in claim 1 wherein, said support means comprises a flexible structure.

16. A monitoring unit comprising:

(a) a pump assembly, said pump assembly comprising a bulb, a self-sealing inlet valve for selectively admitting fluid to said bulb, an inflatable bladder for selectively receiving fluid from said bulb and an exhaust valve for selectively releasing fluid from said inflatable bladder;

(b) a band internally compartmentalized to receive said pump assembly;

(c) sensor means mounted at said inflatable bladder;

(d) housing means attached to said band;

(e) electronic assembly means contained within said housing means;

(f) conductor means electronically connecting said sensor means with said electronic assembly means;

(g) display means connected to said electronic assembly means; and (h) power source means connected to said electronic assembly means.

17. The pump band recited in claim 16 wherein, said sensor means produce first signals representative of a body parameter, said electronic assembly means receive said first signals and operate thereon to produce second signals, and said display means receives said second signals and produces an output display representative of said body parameter.

* * * * *